(12) United States Patent
Bittner et al.

(10) Patent No.: US 11,319,270 B2
(45) Date of Patent: May 3, 2022

(54) PROCESS FOR PREPARING A HYDROXY COMPOUND BY MEANS OF DECARBOXYLATION

(71) Applicant: Covestro Intellectual Property GmbH & Co. KG, Leverkusen (DE)

(72) Inventors: Natalie Bittner, Frechen (DE); Jens Langanke, Mechernich (DE); Niklas Meine, Düsseldorf (DE); Jan Heijl, Lokeren (BE)

(73) Assignee: COVESTRO INTELLECTUAL PROPERTY GMBH & CO. KG, Leverkusen (DE)

( * ) Notice: Subject to any disclaimer, the term of this patent is extended or adjusted under 35 U.S.C. 154(b) by 0 days.

(21) Appl. No.: 17/294,934

(22) PCT Filed: Dec. 2, 2019

(86) PCT No.: PCT/EP2019/083215
§ 371 (c)(1),
(2) Date: May 18, 2021

(87) PCT Pub. No.: WO2020/114928
PCT Pub. Date: Jun. 11, 2020

(65) Prior Publication Data
US 2022/0017441 A1   Jan. 20, 2022

(30) Foreign Application Priority Data
Dec. 7, 2018 (EP) ..................... 18211039

(51) Int. Cl.
| | | |
|---|---|---|
| *C07C 37/50* | (2006.01) | |
| *C07C 68/04* | (2006.01) | |
| *C08G 64/00* | (2006.01) | |
| *B01J 29/08* | (2006.01) | |
| *C07C 37/20* | (2006.01) | |
| *C08G 64/06* | (2006.01) | |

(52) U.S. Cl.
CPC ............ *C07C 37/50* (2013.01); *B01J 29/084* (2013.01); *C07C 37/20* (2013.01); *C07C 68/04* (2013.01); *C08G 64/06* (2013.01)

(58) Field of Classification Search
CPC .......... C07C 37/20; C07C 37/50; C07C 68/04
See application file for complete search history.

(56) References Cited

FOREIGN PATENT DOCUMENTS

| EP | 1277723 A1 | 1/2003 |
|---|---|---|
| EP | 2586767 A1 | 5/2013 |
| JP | 2016023136 | 2/2016 |

OTHER PUBLICATIONS

Koelewijn et al., "Sustainable bisphenols from renewable softwood lignin feedstock for polycarbonates and cyanate ester resins", Green Chemistry, Jan. 2017, pp. 2561-2570.
International Search Report for International Patent Application No. PCT/EP2019/083215, dated Jan. 27, 2020.
Written Opinion for International Patent Application No. PCT/EP2019/083215, dated Jan. 27, 2020.

*Primary Examiner* — Sikarl A Witherspoon
(74) *Attorney, Agent, or Firm* — K&L Gates LLP

(57) ABSTRACT

The invention relates to a process for preparing a specific hydroxy compound by means of decarboxylation of a specific carboxylic acid compound or a salt of said carboxylic acid compound, to a method for preparing a diaryl carbonate, a bisphenol or a polycarbonate, a diaryl carbonate or bisphenol, a polycarbonate, and to a method for adjusting the isotope ratio of C14 to C12 in a polymer. A specific solvent is used during decarboxylation.

18 Claims, No Drawings

PROCESS FOR PREPARING A HYDROXY COMPOUND BY MEANS OF DECARBOXYLATION

CROSS REFERENCE TO RELATED APPLICATIONS

This application is a U.S. national stage application, filed under 35 U.S.C. § 371, of International Application No. PCT/EP2019/083215, which was filed on Dec. 2, 2019, and which claims priority to European Patent Application No. 18211039.5, which was filed on Dec. 7, 2018. The contents of each are hereby incorporated by reference into this specification.

FIELD

The present invention relates to a process for producing a specific hydroxy compound by decarboxylation of a specific carboxylic acid compound or of a salt of said carboxylic acid compound, to a process for producing a diaryl carbonate, a bisphenol or a polycarbonate, to a diaryl carbonate or bisphenol, to a polycarbonate, and to a process for adjusting the C14 to C12 isotope ratio in a polymer.

BACKGROUND

Phenols having different substitution patterns on the aromatic ring are the starting compounds for various monomers and thus also for the polymers resulting therefrom. The production of such phenols from renewable raw materials is a major challenge. One option for producing biobased phenol is the direct fermentation of sugars, as described for example in WO 2014/076113 A1. However, phenol is toxic to the microorganism described therein and its removal from the aqueous fermentation broth is also laborious. Hydroxybenzoic acids such as 4-hydroxybenzoic acid, 2-hydroxybenzoic acid, and 3-hydroxybenzoic acid can likewise be produced from sugars by fermentation. Since they are generally less toxic to the microorganisms used, higher yields can usually be achieved compared to phenol. Hydroxybenzoic acids can be crystallized and separated from the fermentation broth. A subsequent decarboxylation of 4-hydroxybenzoic acid to phenol has also previously been described. JP 2016-23136 A describes the reaction using a heterogeneous catalyst in water as solvent. A. S. Lisitsyn in Applied Catalysis A: General 332; 2007 (166-170) describes decarboxylation in diphenyl ether using a copper catalyst. L. J. Goossen et al. in ChemCatChem 2010, 2, 430-442 describe decarboxylation using a silver or copper catalyst in NMP as solvent. Dalton Transactions (24), 4683-4688; 2009 also describes decarboxylation in toluene.

In order to obtain phenols in a high degree of purity, it is necessary in the methods described in the prior art first to remove the solvent. Often, however, solvent residues remain in the phenol, which makes the further use of said phenol for the production of, for example, monomers such as diaryl carbonates or bisphenols difficult or affects the yield of these processes.

Likewise, when using homogeneous catalysts for the decarboxylation of hydroxybenzoic acid, it is necessary to ensure that the catalyst can be separated from the phenol and—if possible—also recycled.

SUMMARY

The object of the present invention therefore was to provide a process for producing specific hydroxy compounds of the formula (I) by decarboxylation of a carboxylic acid compound of the formula (II) or of a corresponding salt of said carboxylic acid compound of the formula (II), thereby improving at least one disadvantage of the prior art. In particular, the object of the present invention was to provide a process that affords the hydroxy compound of the formula (I) in high purity. This should render the obtained hydroxy compound of the formula (I) suitable in particular for use as a starting material for other chemical compounds. In particular, the hydroxy compound of the formula (I) should be provided by a process in which the workup of the product is as straightforward as possible and as a result preferably cost-effective and environmentally friendly. It was desirable here to use a heterogeneous catalyst, since this already facilitates the separation of the catalyst from the hydroxy compound of the formula (I).

At least one, preferably all, of the abovementioned objects were achieved by the present invention. It was surprisingly found that the decarboxylation of a carboxylic acid compound of the formula (II) or of a corresponding salt of said carboxylic acid compound of the formula (II) can be effectively carried out using a heterogeneous catalyst in a hydroxy compound of the formula (I) as solvent. The yield of the desired hydroxy compound of the formula (I) is preferably even higher than under the conditions described in the prior art. The use of at least one hydroxy compound of the formula (I) as solvent during the decarboxylation reaction offers the particular advantage that a reaction mixture is obtained that can be used directly as starting material for further chemical reactions without laborious workup after separation of the catalyst. This is firstly because the reaction proceeds almost to completion. Secondly, it is not necessary to remove the solvent. The process can particularly preferably be designed such that the solvent used corresponds to the desired hydroxy compound of the formula (I) to be produced. On completion of the decarboxylation and after separation of the catalyst, this affords an almost pure hydroxy compound of the formula (I).

The invention accordingly provides a process for producing a hydroxy compound of the formula (I)

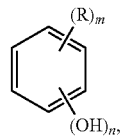

in which
R is a linear or branched alkyl group having 1 to 6 carbon atoms,
n is 1 or 2, and
m is 0, 1, 2, or 3,
by decarboxylation of a carboxylic acid compound of the formula (II) or of a corresponding salt of said carboxylic acid compound of the formula (II)

in which R, n, and m are as defined above,
using at least one heterogeneous catalyst,
characterized in that at least one hydroxy compound of the formula (I) is throughout the decarboxylation reaction present in a stoichiometric excess relative to the carboxylic acid compound of the formula (II), the decarboxylation being carried out at a temperature that is above the melting temperature both of the hydroxy compound of the formula (I) that is formed and of the at least one hydroxy compound of the formula (I) used in a stoichiometric excess.

DETAILED DESCRIPTION

According to the present invention, the carboxylic acid compound of the formula (II) or salt of the carboxylic acid compound of the formula (II) is present alongside at least one hydroxy compound of the formula (I). This also applies before the start of the decarboxylation reaction. The at least one hydroxy compound of the formula (I) is present in a stoichiometric excess. This means that the carboxylic acid compound of the formula (II) or salt of the carboxylic acid compound of the formula (II) is present in a molar deficit relative to the at least one hydroxy compound of the formula (I). During the decarboxylation, the hydroxy compound of the formula (I) is then additionally formed as a target product. This may be the same or different, preferably the same, as the at least one hydroxy compound of the formula (I). The invention thus excludes the situation in which the hydroxy compound of the formula (I) forms in situ as the target product and then at some point thereafter a molar deficit of the carboxylic acid compound of the formula (II) or of the salt of the carboxylic acid compound of the formula (II) potentially develops, since at least one hydroxy compound of the formula (I) must be additionally present from the start of the decarboxylation onwards. In accordance with the invention, it is preferable that, before carrying out the decarboxylation reaction, the carboxylic acid compound of the formula (II) or corresponding salt of the carboxylic acid compound of the formula (II) is dissolved in the at least one hydroxy compound of the formula (I) that throughout the decarboxylation reaction is present in a stoichiometric excess relative to the carboxylic acid compound of the formula (II). The carboxylic acid compound of the formula (II) or salt of the carboxylic acid compound of the formula (II) is thus preferably soluble in the at least one hydroxy compound of the formula (I) that throughout the decarboxylation reaction is present in a stoichiometric excess relative to the carboxylic acid compound of the formula (II). The terms "dissolve" and "in solution" are in accordance with the invention to be understood as having the meanings known to those skilled in the art. The terms "dissolve" and "in solution" preferably mean that, when filtering a liquid in which a substance is dissolved, no solid can be separated off using customary filter methods.

The process of the invention is executed at a temperature that is above the melting temperature both of the hydroxy compound of the formula (I) that is formed and of the at least one hydroxy compound of the formula (I) used in a stoichiometric excess. The process of the invention is thus preferably executed in solution. The at least one hydroxy compound of the formula (I) that throughout the decarboxylation reaction is present in a stoichiometric excess relative to the carboxylic acid compound of the formula (II) serves here as the solvent.

The process of the invention is preferably executed at a temperature of 100 to 400° C., particularly preferably at 150 to 300° C., and very particularly preferably from 160 to 250° C.

The process of the invention can be a batch process, semi-batch process or continuous process.

The process of the invention is preferably used for producing a hydroxy compound of the formula (I) shown above, in which R is a tert-butyl, propyl or methyl group, n is 1 or 2, preferably 1, and m is 0, 1, 2 or 3. The process of the invention is particularly preferably used to produce 4-propylphenol, ortho-, para- or meta-methylphenol (cresols), 2,4-dimethylphenol, 2,5-dimethylphenol, 4-tert-butylphenol or phenol. The process of the invention is very particularly preferably characterized in that the hydroxy compound of the formula (I) is phenol.

It is also preferable that the at least one hydroxy compound of the formula (I) that throughout the decarboxylation reaction is present in a stoichiometric excess relative to the carboxylic acid compound of the formula (II) is a hydroxy compound of the formula (I) shown above, in which R is a tert-butyl, propyl or methyl group, n is 1 or 2, preferably 1, and m is 0, 1, 2 or 3. This at least one hydroxy compound of the formula (I) that throughout the decarboxylation reaction is present in a stoichiometric excess relative to the carboxylic acid compound of the formula (II) is particularly preferably 4-propylphenol, ortho-, para- or meta-methylphenol (cresols), 2,4-dimethylphenol, 2,5-dimethylphenol, 4-tert-butyl-phenol or phenol. Very particular preference is given to phenol.

It is preferable that the hydroxy compound of the formula (I) produced by the process of the invention corresponds to the hydroxy compound of the formula (I) that throughout the decarboxylation reaction is present in a stoichiometric excess relative to the carboxylic acid compound of the formula (II).

In accordance with the invention, the carboxylic acid compound of the formula (II) or salt of the carboxylic acid compound of the formula (II) are occasionally also collectively referred to as the carboxylic acid compound of the formula (II). However, unless otherwise stated, this always means the free acid and/or the salt. According to the invention, it is also possible to use mixtures of different carboxylic acid compounds of the formula (II) or of different salts of the carboxylic acid compounds of the formula (II) or else mixtures of at least one carboxylic acid compound of the formula (II) with at least one salt of the carboxylic acid compound of the formula (II).

In the process of the invention it is preferable that the cation of the salt of the carboxylic acid compound of the formula (II) is selected from the group consisting of alkali metal cations, alkaline earth metal cations, ammonium, phosphonium, cations of manganese, iron, cobalt, nickel, copper, zinc, molybdenum, cadmium, and any desired mixtures thereof. The cation of the salt of the carboxylic acid compound of the formula (II) is particularly preferably selected from the group consisting of alkali metal cations, alkaline earth metal cations, and mixtures thereof.

In addition, it is preferable according to the invention that the carboxylic acid compound of the formula (II) or corresponding salt of the carboxylic acid compound of the formula (II) is selected from the group consisting of 2-hydroxybenzoic acid, 4-hydroxybenzoic acid, and the corresponding salts. Very particular preference is given to 4-hydroxybenzoic acid or the corresponding salt.

All heterogeneous catalysts that are active in a decarboxylation reaction are in principle suitable as catalyst in the process of the invention. These are known to those skilled in the art. The heterogeneous catalyst used in the process of the invention is preferably selected from the group consisting of $Al_2O_3$, $H_3PO_4$ supported on $Al_2O_3$, $PtCl_x$ supported on $Al_2O_3$, Cu/Al/Ga-MOFs, Pt—Al-MOFs, palladium supported on activated carbon, platinum supported on activated carbon, zeolites such as ZSM-5, HZSM-5, $Fe_2O_3$ supported on MCM-41 (Mobil Composition of Matter No. 41), $Fe_2O_3$ supported on Al-MCM-41, Pt supported on SAPO-34 (silicoaluminophosphate), Pt supported on SAPO-11, Pt hydrotalcite, Pt supported on $SiO_2$, and any desired mixtures thereof. The process of the invention is particularly preferably characterized in that the at least one heterogeneous catalyst is a zeolite. The process of the invention is very particularly preferably characterized in that the zeolite has a faujasite structure.

Zeolites and in particular zeolites having a faujasite structure are known to those skilled in the art. The crystal structure of faujasite is identical to that of the synthetic zeolite Y. The basic element of the faujasite framework are sodalite cages, which are connected to one another via hexagonal prisms. Very particular preference is given to the zeolite type Y catalyst used according to the invention.

In one aspect of the invention, it is further preferable that the carboxylic acid compound of the formula (II) or corresponding salt of the carboxylic acid compound of the formula (II) was obtained by fermentation or from sugars, lignocellulose, lignocellulose-containing materials, furans, and/or lignin. The carboxylic acid compound of the formula (II) or corresponding salt of the carboxylic acid compound of the formula (II) is thus preferably biobased. For the purposes of the present invention, the expression "biobased" is understood as meaning that the relevant chemical compound is at the filing date available and/or obtainable via a renewable and/or sustainable raw material and/or preferably is such a renewable and/or sustainable raw material. A renewable and/or sustainable raw material is preferably understood as meaning a raw material that is regenerated by natural processes at a rate that is comparable to its rate of depletion (see CEN/TS 16295:2012). The expression is used in particular to differentiate it from raw materials produced from fossil raw materials, also referred to in accordance with the invention as petroleum-based. Whether a raw material is biobased or petroleum-based can be determined by the measurement of carbon isotopes in the raw material, since the relative amounts of the carbon isotope C14 are lower in fossil raw materials. This can be done, for example, in accordance with ASTM D6866-18 (2018) or 15016620-1 to -5 (2015) or DIN SPEC 91236 2011-07.

In accordance with the invention, the term "petroleum-based" is preferably used to describe those compounds that have a C14 isotope content of less than $0.3 \times 10^{-12}$, particularly preferably of $0.2 \times 10^{-12}$, and very particularly preferably of $0.1 \times 10^{12}$. If the hydroxy compound of the formula (I) is phenol, a petroleum-based phenol is preferably obtained via the Hock process.

Those skilled in the art know how to obtain the carboxylic acid compound of the formula (II) or corresponding salt of the carboxylic acid compound of the formula (II) by fermentation or from sugars, lignocellulose, lignocellulose-containing materials, furans, and/or lignin.

This is described for example in WO 2015174446, WO 2015156271, US20040143867, Appl. Environ Microbiol 84 2018:e02587-17, WO2016114668, Biomass and Bioenergy 93:209-216 October 2016, Biotechnol Bioeng. 2016 July; 113(7):1493-503, ACS Catal., 2016, 6 (9), pp. 6141-6145 or Biotechnol. Bioeng., 113: 1493-1503, Appl Microbiol Biotechnol. 2018 October; 102(20):8685-8705, Microbiology. 1994 April; 140 (Pt 4):897-904, Journal of Biotechnology 132 (2007) 49-56, WO2000018942, U.S. Pat. No. 6,030,819, EP2698435, Bioprocess Biosyst Eng (2017) 40: 1283, U.S. Pat. Nos. 2,996,540, 9,206,449, Nature 2014, 515, 249-252, Biomass and Bioenergy 93 (2016) 209-216, 3 Biotech. 2015 October; 5(5): 647-651, Appl Environ Microbiol. 2018 Mar. 15; 84(6): e02587-17, U.S. Pat. No. 3,360, 553A.

In this aspect of the invention, it is particularly advantageous that the use of a biobased carboxylic acid compound of the formula (II) or of a corresponding salt of the carboxylic acid compound of the formula (II) affords a biobased hydroxy compound of the formula (I). This can in turn be used to produce further biobased compounds, for example diaryl carbonates, bisphenols or polycarbonates, ultimately providing access to biobased polymers and allowing them to be produced in an efficient and cost-effective way.

The present invention therefore in a further aspect relates to a process for producing a diaryl carbonate, a bisphenol or a polycarbonate, characterized in that, in the production of the diaryl carbonate, of the bisphenol or of the polycarbonate, the direct process product of the process of the invention in all preferences and preferred combinations is used after removal of the heterogeneous catalyst. As already set out above, the process of the invention makes it possible, after carrying out the decarboxylation, to obtain a mixture that contains the produced hydroxy compound of the formula (I) and the at least one hydroxy compound of the formula (I) that throughout the decarboxylation reaction is present in a stoichiometric excess relative to the carboxylic acid compound of the formula (II). These two hydroxy compounds can preferably be identical. On removing the catalyst from this mixture, an essentially pure mixture of the hydroxy compounds of the formula (I) is present. This can without further laborious purification steps be fed into the process of the invention for the production of a diaryl carbonate, a bisphenol or a polycarbonate. The separation of the catalyst is known to those skilled in the art. It can be achieved for example by filtration. The expression "direct process product" is therefore to be understood in particular as meaning that no prior removal of solvent from the process product is necessary. Since this removal of a solvent is usually associated with thermal stress, the mixture according to the invention of the hydroxy compound of the formula (I) was thus subjected to less thermal stress than corresponding compounds of the prior art.

According to the invention, it is in this situation particularly preferable that the carboxylic acid compound of the formula (II) or salt of the carboxylic acid compound of the formula (II) is 4-hydroxybenzoic acid or the corresponding salt.

Processes for producing diaryl carbonates or bisphenols are known to those skilled in the art. Diaryl carbonates can be produced for example by reacting the hydroxy compound of the formula (I) with a carbonyl halide, preferably phosgene, with carbon monoxide or with dimethyl carbonate in a known manner. Bisphenols can be obtained by reacting the hydroxy compound of the formula (I) with a ketone or an aldehyde in a known manner Processes for producing polycarbonates using the hydroxy compound of the formula (I) are also known to those skilled in the art. For example, the hydroxy compound of the formula (I) can be used as a chain terminator in an interfacial process for producing polycarbonate in a known manner.

In these processes, the other reactants, such as the ketones or aldehydes, can likewise be biobased or petroleum-based, preferably biobased.

In addition, it is in this process preferable that, in the process of the invention for the production of a hydroxy compound of the formula (I) in all preferences and combinations described above, the carboxylic acid compound of the formula (II) or corresponding salt of the carboxylic acid compound of the formula (II) was obtained by fermentation or from sugars, lignocellulose, furans, and/or lignin, and that, in the process of the invention for the production of a hydroxy compound of the formula (I) in all preferences and combinations described above, the at least one hydroxy compound of the formula (I) that throughout the decarboxylation reaction is present in a stoichiometric excess relative to the carboxylic acid compound of the formula (II) is petroleum-based or that, in the process of the invention for the production of a hydroxy compound of the formula (I) in all preferences and combinations described above, the carboxylic acid compound of the formula (II) or corresponding salt of the carboxylic acid compound of the formula (II) is petroleum-based, and that, in the process of the invention for the production of a hydroxy compound of the formula (I) in all preferences and combinations described above, the at least one hydroxy compound of the formula (I) that throughout the decarboxylation reaction is present in a stoichiometric excess relative to the carboxylic acid compound of the formula (II) was obtained by fermentation or from sugars, lignocellulose, furans, and/or lignin. This means that it is preferable according to the invention that a mixture of a petroleum-based hydroxy compound of the formula (I) with a biobased hydroxy compound of the formula (I) is obtained. It is possible here either for the hydroxy compound of the formula (I) produced according to the invention to be biobased and then the hydroxy compound of the formula (I) used as solvent to be petroleum-based, or vice versa. This preference is referred to below as Embodiment 2.

There are currently different labels according to the point from which a product may be described as "biobased" (see inter alia the certification program for "biobased" products according to ASTM D6866-18 (2018) or 15016620-1 to -5 (2015) or DIN SPEC 91236 2011-07 from TÜV Rheinland®). The requirement for these different labels is a certain percentage of biobased carbon in the product. The process of the invention makes it possible to easily adjust the proportion of biobased carbon with no disruption to the process of the invention. This can be done simply through addition or exchange of the carboxylic acid compound of the formula (II) or of the source thereof, or of the at least one hydroxy compound of the formula (I) that throughout the decarboxylation reaction is present in a stoichiometric excess relative to the carboxylic acid compound of the formula (II), or of the source thereof. Thus, the process of the invention also makes it possible for existing systems to respond to future changes in labeling requirements without additional outlay. This means that, even with stringent requirements, it will always still be possible to easily produce a hydroxy compound of the formula (I) having the appropriate label as biobased.

It is particularly advantageous when the process of the invention for the production of diaryl carbonates, bisphenols or polycarbonates is characterized in that the hydroxy compound of the formula (I) that had not reacted in the reaction to produce the diaryl carbonate, bisphenol or polycarbonate is separated from the diaryl carbonate, bisphenol or polycarbonate and then fed back into the process of the invention for the production of a hydroxy compound of the formula (I) in all preferences and combinations described above as the hydroxy compound of the formula (I) that throughout the decarboxylation reaction is present in a stoichiometric excess relative to the carboxylic acid compound of the formula (II) This process regime is overall particularly favorable, since the unreacted hydroxy compound of the formula (I) can be reused as a solvent. This is advantageous from ecological and economic viewpoints. This recycling of the hydroxy compound of the formula (I) is particularly preferably carried out in the process of the invention for the production of diaryl carbonates or bisphenols.

When the unreacted hydroxy compound of the formula (I) is a specific mixture of biobased and petroleum-based hydroxy compound, those skilled in the art can take appropriate measures in the process of the invention for the production of a hydroxy compound of the formula (I), in order to further maintain this ratio. For example, they can add to the unreacted hydroxy compound of the formula (I) more of the appropriately sourced at least one hydroxy compound of the formula (I) that throughout the decarboxylation reaction is present in a stoichiometric excess relative to the carboxylic acid compound of the formula (II).

Separation of the unreacted hydroxy compound of the formula (I) from the diaryl carbonate or bisphenol is known to those skilled in the art. It can be effected in a known manner, for example by distillation.

In a further aspect, the invention provides a diaryl carbonate, bisphenol or polycarbonate characterized in that it was obtained by the process of the invention for the production of diaryl carbonates, bisphenols or polycarbonates according to Embodiment 2 in all preferences and combinations. As already described above, these diaryl carbonates, bisphenols or polycarbonates have a specifically adjustable ratio of biobased and petroleum-based carbon. This is accessible by the process of the invention.

Preferred bisphenols of the present invention are those of the formula (2a)

$$HO-Z-OH \qquad (2a),$$

in which

Z is an aromatic radical having 6 to 30 carbon atoms that may contain one or more aromatic rings, may be substituted, and may contain aliphatic or cycloaliphatic radicals or alkylaryls or heteroatoms as bridging elements.

Z in formula (2a) is preferably a radical of the formula (3)

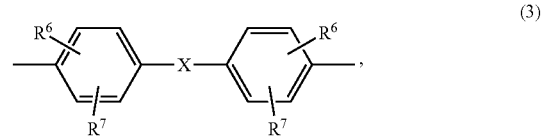

in which $R^6$ and $R^7$ are independently H, $C_1$ to $C_{18}$ alkyl, $C_1$ to $C_{18}$ alkoxy, halogen such as Cl or Br or are each optionally substituted aryl or aralkyl, preferably H or $C_1$ to $C_{12}$ alkyl, particularly preferably H or $C_1$ to $C_8$ alkyl, and very particularly preferably H or methyl, and X is a single bond, $-SO_2-$, $-CO-$, $-O-$, $-S-$, $C_1$ to $C_6$ alkylene, $C_2$ to $C_5$ alkylidene or $C_5$ to $C_6$ cycloalkylidene, which may be substituted by $C_1$ to $C_6$ alkyl, preferably methyl or ethyl, or else $C_6$ to $C_{12}$ arylene, which may optionally be fused with further heteroatom-containing aromatic rings.

X is preferably a single bond, $C_1$ to $C_5$ alkylene, $C_2$ to $C_5$ alkylidene, $C_5$ to $C_6$ cycloalkylidene, —O—, —SO—, —CO—, —S—, —SO$_2$— or is a radical of the formula (3a)

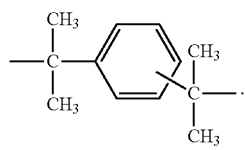
(3a)

Examples of bisphenols are: dihydroxybenzenes, dihydroxydiphenyls, bis(hydroxyphenyl)alkanes, bis(hydroxyphenyl)cycloalkanes, bis(hydroxyphenyl)aryls, bis(hydroxyphenyl) ethers, bis(hydroxyphenyl) ketones, bis(hydroxyphenyl) sulfides, bis(hydroxyphenyl) sulfones, bis(hydroxyphenyl) sulfoxides, 1,1'-bis(hydroxyphenyl)diisopropylbenzenes, and the ring-alkylated and ring-halogenated compounds thereof.

Preferred bisphenols are 4,4'-dihydroxydiphenyl, 2,2-bis(4-hydroxyphenyl)-1-phenylpropane, 1,1-bis(4-hydroxyphenyl)phenylethane, 2,2-bis(4-hydroxyphenyl)propane, 2,4-bis(4-hydroxyphenyl)-2-methylbutane, 1,3-bis[2-(4-hydroxyphenyl)-2-propyl]benzene (bisphenol M), 2,2-bis(3-methyl-4-hydroxyphenyl)propane, bis(3,5-dimethyl-4-hydroxyphenyl)methane, 2,2-bis(3,5-dimethyl-4-hydroxyphenyl)propane, bis(3,5-dimethyl-4-hydroxyphenyl) sulfone, 2,4-bis(3,5-dimethyl-4-hydroxyphenyl)-2-methylbutane, 1,3-bis[2-(3,5-dimethyl-4-hydroxyphenyl)-2-propyl]benzene, and 1,1-bis(4-hydroxyphenyl)-3,3,5-trimethylcyclohexane (bisphenol TMC).

Particularly preferred bisphenols are 4,4'-dihydroxydiphenyl, 1,1-bis(4-hydroxyphenyl)phenylethane, 2,2-bis(4-hydroxyphenyl)propane, 2,2-bis(3,5-dimethyl-4-hydroxyphenyl)propane, 1,1-bis(4-hydroxyphenyl)cyclohexane and 1,1-bis(4-hydroxyphenyl)-3,3,5-trimethylcyclohexane (bisphenol TMC).

Preferred diaryl carbonates of the present invention are those of the formula (2)

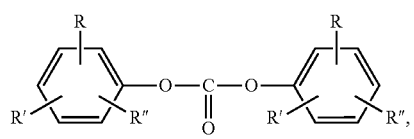
(2)

where R, R' and R" may each independently be the same or different and are hydrogen, optionally branched C1-C34 alkyl, C7-C34 alkylaryl or C6-C34 aryl; in addition R can also denote —COO—R''', where R''' is optionally branched C1-C34 alkyl, C7-C34 alkylaryl or C6-C34 aryl. Such diaryl carbonates are described for example in EP-A 1 609 818. Preference is given to diphenyl carbonate, 4-tert-butylphenyl phenyl carbonate, di(4-tert-butylphenyl) carbonate, biphenyl-4-yl phenyl carbonate, di(biphenyl-4-yl) carbonate, 4-(1-methyl-1-phenylethyl)phenyl phenyl carbonate, and di[4-(1-methyl-1-phenylethyl)phenyl] carbonate. Very particular preference is given to substituted or unsubstituted, preferably unsubstituted, diphenyl carbonate.

The invention further provides a polycarbonate obtained by polymerization of the diaryl carbonate and/or bisphenol of the invention.

Such processes for producing polycarbonate by polymerization of diaryl carbonates and/or bisphenols are known to those skilled in the art. For example, the bisphenols and any branching agents can be dissolved in an aqueous alkaline solution and reacted with a carbonate source optionally dissolved in a solvent, in particular a carbonyl halide such as phosgene, with carbon monoxide or with dimethyl carbonate in a two-phase mixture of an aqueous alkaline solution, an organic solvent, and a catalyst, preferably an amine compound. The reaction regime can also take place in more than one step. Such processes for producing polycarbonate are in principle known as two-phase interfacial processes, for example from H. Schnell, Chemistry and Physics of Polycarbonates, Polymer Reviews, vol. 9, Interscience Publishers, New York 1964 p. 33 ff. and from Polymer Reviews, vol. 10, "Condensation Polymers by Interfacial and Solution Methods", Paul W. Morgan, Interscience Publishers, New York 1965, chapter VIII, p. 325, and the essential conditions are therefore familiar to those skilled in the art.

Alternatively, the polycarbonates according to the invention can also be produced by the melt transesterification process. The melt transesterification process is described for example in the Encyclopedia of Polymer Science, vol. 10 (1969), Chemistry and Physics of Polycarbonates, Polymer Reviews, H. Schnell, vol. 9, John Wiley and Sons, Inc. (1964) and in DE-C 10 31 512. In the melt transesterification process, the bisphenols are transesterified in the melt with diaryl carbonates using suitable catalysts and optionally other additives.

In a further aspect, the present invention provides a process for adjusting the $C_{14}$ to $C_{12}$ isotope ratio in a polymer, preferably polycarbonate, characterized in that the process comprises the following steps:

(a1) executing the process of the invention for the production of a hydroxy compound of the formula (I) in all preferences and combinations described above, wherein a molar ratio of the hydroxy compound of the formula (I) that throughout the decarboxylation reaction is present in a stoichiometric excess relative to the carboxylic acid compound of the formula (II), and that is petroleum-based, to the hydroxy compound of the formula (I) as process product of the process according to the process of the invention is maintained, (b1) optionally altering the molar ratio from process step (a1) through the addition either of a hydroxy compound of the formula (I) that is petroleum-based or of a hydroxy compound of the formula (I) obtained by fermentation or from sugars, lignocellulose, furans, and/or lignin, (c1) producing a diaryl carbonate or bisphenol using the mixture of hydroxy compounds of the formula (I) obtained in process step (b1), and (d1) producing a polymer, preferably polycarbonate, using at least one diaryl carbonate and/or bisphenol from process step (c1).

As already described in more detail above, those skilled in the art know that the C14 and C12 isotope ratio in a polymer is an indicator of whether a polymer can be described as biobased or not. Methods for the determination of these isotopes and thus also of the ratio have already been described above. The isotope ratio is preferably determined in accordance with ASTM D6866-18 (2018) or ISO16620-1 to -5 (2015) or DIN SPEC 91236 2011-07. Likewise, for process step (c1) and also (d1), reference is made to the preferred bisphenols and diaryl carbonates already described above and to the processes for the polymerization thereof to obtain a polycarbonate. This process of the invention also makes it possible for existing systems to respond to future changes in labeling requirements without additional outlay. This means that, even with stringent requirements, it will always still be possible to easily produce polymer, preferably polycarbonate, having the appropriate label as biobased.

Another subject of the present invention is a process for producing a bisphenol, comprising the following steps:
- (a2) executing the process of the invention for the production of a hydroxy compound of the formula (I), wherein a hydroxy compound of the formula (I) is obtained,
- (b2) reacting the hydroxy compound of the formula (I) from step (a2) with a ketone or an aldehyde to afford a bisphenol.

An additional subject of the present invention is a process for producing a diaryl carbonate, comprising the following steps:
- (a3) executing the process of the invention for the production of a hydroxy compound of the formula (I), wherein a hydroxy compound of the formula (I) is obtained,
- (b3) reacting the hydroxy compound of the formula (I) from step (a3) with a carbonyl halide, with carbon monoxide or with dimethyl carbonate to afford a diaryl carbonate.

A further subject of the present invention is a process for producing a polycarbonate, comprising the following steps:
- (a4) executing the process of the invention for the production of a bisphenol, wherein a bisphenol is obtained,
- (b4) reacting the bisphenol from step (a4) with a carbonyl halide, with carbon monoxide or with dimethyl carbonate to afford a polycarbonate.

Another further subject of the present invention is a process for producing a polycarbonate, comprising the following steps:
- (a5) executing the process of the invention for the production of a diaryl carbonate, wherein a diaryl carbonate is obtained,
- (b5) reacting the diaryl carbonate from step (a5) with a bisphenol to afford a polycarbonate.

Yet another further subject of the present invention is a process for producing a polycarbonate, comprising the following steps:
- (a6) executing the process of the invention for the production of a bisphenol, wherein a bisphenol is obtained,
- (b6) executing the process of the invention for the production of a diaryl carbonate, wherein a diaryl carbonate is obtained,
- (c6) reacting the bisphenol from step (a6) with a diaryl carbonate from step (b6) to afford a polycarbonate.

The present invention is realized through all these above subjects.

Examples

Abbreviations:
bara: Absolute pressure in bar
rpm: Revolutions per minute
$^1$H NMR: Proton resonance spectroscopy
M: Molar concentration in mol/L
aq.: Aqueous solution Chemicals:
4-Hydroxybenzoic acid (4-HBA): Purity ≥99%, Sigma-Aldrich Chemie GmbH
DM water ($H_2O$): Demineralized water from the piped supply
Sodium hydroxide (NaOH): Anhydrous, purity ≥97%, Sigma-Aldrich Chemie GmbH
aq. NaOH solution prepared from demineralized water and sodium hydroxide
Phenol: Purity ≥96%, Sigma-Aldrich Chemie GmbH
Hexadeuterodimethyl sulfoxide (DMSO-d6): Purity ≥96%, Euriso-Top GmbH Catalysts:
CBV 600 (CAS 1318-02-1), Zeolyst International, Inc., surface area 660 $m^2$/g, pore size 2.43 nm, Si/Al ratio 2.5. The catalyst was calcined prior to use at 300° C. in air for 3 h.
Faujasite (product reference: BCR704), Sigma-Aldrich Chemie GmbH, surface area 567 $m^2$/g, pore size 0.67 nm, Si/Al ratio 1.6. The catalyst was used as received.

General Experimental Procedure—Experiments with Catalyst:

A 10 mL pressure reactor was charged with 0.5 g of 4-hydroxybenzoic acid, 0.5 mL of solvent (see table), and 0.02 g of the respective catalyst (see table), flushed with argon as inert gas, and the reactor was closed. The reactor was then pressurized with argon to 3 bara, the mixture was stirred at 800 rpm for 10 min, and the pressure was released to 1.5 bara. This operation was repeated one more time before the reactor was brought to the reaction temperature of 230° C. After the appropriate reaction time (see table) at this temperature, the pressure reactor was cooled to room temperature and the pressure released. The reaction mixture obtained was taken up in ethanol, the solid catalyst was separated off by centrifugation (5 min, 5000 rpm, Hettich Universal 320), and the solution was freed of ethanol on a rotary evaporator. The reaction product thus isolated was then investigated by $^1$H-NMR.

General Experimental Procedure—Experiments without Catalyst:

The procedure was analogous to the general experimental procedure for experiments with a catalyst. The sole difference was that a catalyst was not used.

$^1$H NMR for the Determination of 4-Hydroxybenzoic Acid and Phenol in the Reaction Product:

About 100 mg of the reaction product obtained was dissolved in 0.5 mL of DMSO-d6 and a $^1$H-NMR spectrum was recorded at 400 MHz on a Bruker Avance 400. The spectra obtained were evaluated on the basis of the specific shifts and integrals shown below.

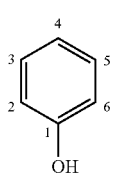 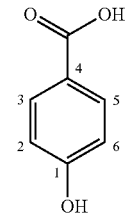

Phenol- $^1$H NMR (400 MHz, DMSO-d6): δ (ppm) 9.4 ($C_{OH}$, 1H), 7.10-7.20 ($C_{3,5}$, 2H), 6.72-6.78 ($C_{2,4,6}$, 3H)

4-Hydroxybenzoic acid- $^1$H NMR (400 MHz, DMSO-d6): δ (ppm) 12.3 ($C_{OOH}$, 1H) 10.1 ($C_{OH}$, 1H), 7.8 ($C_{3,5}$, 2H), 6.80-6.86 ($C_{2,6}$, 2H)

TABLE 1

| # | Catalyst | Solvent | Reaction time [h] | Reaction product [molar ratio from $^1$H NMR] |
|---|----------|---------|---|---|
| 1 | Faujasite | H$_2$O | 2 | 2:1 Phenol/4-hydroxybenzoic acid |
| 2 | Faujasite | Phenol | 2 | Phenol |
| 3 | CBV 600 | H$_2$O | 2 | 2:1 Phenol/4-hydroxybenzoic acid |
| 4 | CBV 600 | Phenol | 2 | 3:1 Phenol/4-hydroxybenzoic acid $^a$ |
| 5 | — | H$_2$O | 2 | 1:1 Phenol/4-hydroxybenzoic acid |

$^a$ The reported molar ratio refers only to the phenol formed.

As can be seen from the table, through the use of a hydroxy compound of the formula (I) (phenol in the examples) it is possible, under otherwise identical conditions, to increase conversion to the desired product in relation to water as solvent. This applies to various heterogeneous catalysts.

What is claimed is:

1. A process for producing a hydroxy compound of the formula (I)

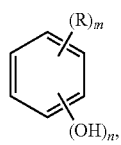

(I)

in which
R is a linear or branched alkyl group having 1 to 6 carbon atoms,
n is 1 or 2, and
m is 0, 1, 2, or 3, by decarboxylation of a carboxylic acid compound of the formula (II) or of a corresponding salt of said carboxylic acid compound of the formula (II)

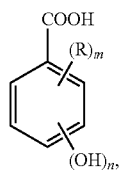

(II)

in which R, n, and m are as defined above,
using at least one heterogeneous catalyst, wherein the at least one hydroxy compound of the formula (I) is throughout the decarboxylation reaction present in a stoichiometric excess relative to the carboxylic acid compound of the formula (II), the decarboxylation being carried out at a temperature that is above the melting temperature both of the hydroxy compound of the formula (I) that is formed and of the at least one hydroxy compound of the formula (I) used in a stoichiometric excess.

2. The process as claimed in claim 1, wherein, before carrying out the decarboxylation reaction, the carboxylic acid compound of the formula (II) or corresponding salt of the carboxylic acid compound of the formula (II) is dissolved in the at least one hydroxy compound of the formula (I) that throughout the decarboxylation reaction is present in a stoichiometric excess relative to the carboxylic acid compound of the formula (II).

3. The process as claimed in claim 1, wherein the at least one heterogeneous catalyst is a zeolite.

4. The process as claimed in claim 3, wherein the zeolite has a faujasite structure.

5. The process as claimed in claim 1, wherein the cation of the salt of the carboxylic acid compound of the formula (II) is selected from the group consisting of alkali metal cations, alkaline earth metal cations, ammonium, phosphonium, cations of manganese, iron, cobalt, nickel, copper, zinc, molybdenum, cadmium, and any desired mixtures thereof.

6. The process as claimed in claim 1, wherein the carboxylic acid compound of the formula (II) or corresponding salt of the carboxylic acid compound of the formula (II) was obtained by fermentation or from sugars, lignocellulose, lignocellulose-containing materials, furans, and/or lignin.

7. The process as claimed in claim 1, wherein the produced hydroxy compound of the formula (I) corresponds to the hydroxy compound of the formula (I) that throughout the decarboxylation reaction is present in a stoichiometric excess relative to the carboxylic acid compound of the formula (II).

8. The process as claimed in claim 1, wherein the hydroxy compound of the formula (I) is phenol.

9. The process as claimed in claim 1, wherein the carboxylic acid compound of the formula (II) or corresponding salt of the carboxylic acid compound of the formula (II) is selected from the group consisting of 2-hydroxybenzoic acid, 4-hydroxybenzoic acid, and the corresponding salts.

10. A process comprising:
(a1) executing the process as claimed in claim 1, wherein a molar ratio of the hydroxy compound of the formula (I) that throughout the decarboxylation reaction is present in a stoichiometric excess relative to the carboxylic acid compound of the formula (II), and that is petroleum-based, to the hydroxy compound of the formula (I) as process product of the process as claimed in claim 1 is maintained.

11. A process for producing a bisphenol, wherein the process comprises:
(a2) executing the process as claimed in claim 1 for the production of a hydroxy compound of the formula (I), wherein a hydroxy compound of the formula (I) is obtained,
(b2) reacting the hydroxy compound of the formula (I) from step (a2) with a ketone or an aldehyde to afford a bisphenol.

12. A process for producing a diaryl carbonate, wherein the process comprises:
(a3) executing the process as claimed in claim 1 for the production of a hydroxy compound of the formula (I), wherein a hydroxy compound of the formula (I) is obtained,
(b3) reacting the hydroxy compound of the formula (I) from step (a3) with a carbonyl halide, with carbon monoxide or with dimethyl carbonate to afford a diaryl carbonate.

13. A process for producing a polycarbonate, wherein the process comprises:
(a4) executing the process as claimed in claim 11 for the production of a bisphenol, wherein a bisphenol is obtained, (b4) reacting the bisphenol from step (a4) with a carbonyl halide, with carbon monoxide or with dimethyl carbonate to afford a polycarbonate.

14. A process for producing a polycarbonate, wherein the process comprises:
- (a5) executing the process as claimed in claim 12 for the production of a diaryl carbonate, wherein a diaryl carbonate is obtained,
- (b5) reacting the diaryl carbonate from step (a5) with a bisphenol to afford a polycarbonate.

15. A process for producing a polycarbonate, wherein the process comprises:
- (a6) executing a process for the production of a bisphenol, wherein a bisphenol is obtained, the process for producing a bisphenol comprising:
  - (a2) executing the process as claimed in claim 1 for the production of a hydroxy compound of the formula (I), wherein a hydroxy compound of the formula (I) is obtained,
  - (b2) reacting the hydroxy compound of the formula (I) from step (a2) with a ketone or an aldehyde to afford a bisphenol,
- (b6) executing a process for the production of a diaryl carbonate, wherein a diaryl carbonate is obtained, the process for producing a diaryl carbonate comprising:
  - (a3) executing the process as claimed in claim 1 for the production of a hydroxy compound of the formula (I), wherein a hydroxy compound of the formula (I) is obtained,
  - (b3) reacting the hydroxy compound of the formula (I) from step (a3) with a carbonyl halide, with carbon monoxide or with dimethyl carbonate to afford a diaryl carbonate,
- (c6) reacting the bisphenol from step (a6) with the diaryl carbonate from step (b6) to afford a polycarbonate.

16. The process as claimed in claim 10, wherein the polymer is a polycarbonate.

17. A process for adjusting a C14 to C12 isotope ratio in a polymer, the process comprising:
- (b1) altering the molar ratio from process step (a1) as claimed in claim 10 through the addition either of a hydroxy compound of the formula (I) that is petroleum-based or of a hydroxy compound of the formula (I) obtained by fermentation or from sugars, lignocellulose, furans, and/or lignin;
- (c1) producing a diaryl carbonate or bisphenol using the mixture of hydroxy compounds of the formula (I) obtained in process step (b1); and
- (d1) producing the polymer using at least one diaryl carbonate and/or bisphenol from process step (c1).

18. A process as claimed in claim 17, wherein the polymer produced in process step (d1) is a polycarbonate.

* * * * *